United States Patent
Iwamoto et al.

(10) Patent No.: US 7,432,507 B2
(45) Date of Patent: Oct. 7, 2008

(54) PLASTIC IDENTIFYING APPARATUS AND PLASTIC IDENTIFYING METHOD

(75) Inventors: Hiroshi Iwamoto, Toyonaka (JP); Takao Hisazumi, Ibaraki (JP); Toshiaki Koga, Hirakata (JP); Yuji Maniwa, Nagaokakyo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 244 days.

(21) Appl. No.: 10/563,402

(22) PCT Filed: Jul. 15, 2004

(86) PCT No.: PCT/JP2004/010433

§ 371 (c)(1),
(2), (4) Date: Jan. 4, 2006

(87) PCT Pub. No.: WO2005/015174

PCT Pub. Date: Feb. 17, 2005

(65) Prior Publication Data

US 2006/0157650 A1      Jul. 20, 2006

(30) Foreign Application Priority Data

Jul. 18, 2003    (JP) .............................. 2003-276845

(51) Int. Cl.
- *G01J 5/00* (2006.01)
- *B07C 5/10* (2006.01)
- *B07C 5/342* (2006.01)

(52) U.S. Cl. ...................... 250/338.1; 209/524; 209/587

(58) Field of Classification Search .............. 250/338.1, 250/339.21, 341.8; 209/522, 523, 524, 577, 209/587

See application file for complete search history.

(56) References Cited

U.S. PATENT DOCUMENTS

| | | | | |
|---|---|---|---|---|
| 4,314,645 A | * | 2/1982 | Perkins et al. | 209/638 |
| 4,597,487 A | * | 7/1986 | Crosby et al. | 194/209 |
| 4,852,029 A | * | 7/1989 | Pope et al. | 702/41 |
| 5,779,026 A | * | 7/1998 | Hosch et al. | 198/817 |
| 2002/0179503 A1 | * | 12/2002 | Yap | 209/657 |
| 2003/0136649 A1 | * | 7/2003 | Tvinnereim et al. | 198/841 |
| 2003/0155511 A1 | | 8/2003 | Hisazui et al. | |
| 2004/0069947 A1 | * | 4/2004 | Iwamoto et al. | 250/341.8 |

FOREIGN PATENT DOCUMENTS

| | | |
|---|---|---|
| JP | 2003-202291 | 7/2003 |
| JP | 2002-286637 | 10/2003 |
| WO | 03/038412 | 5/2003 |

* cited by examiner

*Primary Examiner*—David P. Porta
*Assistant Examiner*—David S Baker
(74) *Attorney, Agent, or Firm*—Hamre, Schumann, Mueller & Larson, P.C.

(57) ABSTRACT

A plastic identifying apparatus according to the present invention identifies the kind of plastic in an object to be identified by using as an identification face at least two faces of a test piece (1) serving as the object to be identified. The plastic identifying apparatus according to the present invention includes an identifying and detecting portion (3, 4) for identifying the kind of the plastic included in the test piece (1) and a toppling system (7a, 7b) for toppling the test piece (1) by applying an external force to the test piece (1) in order to change the identification face of the test piece (1) facing the identifying and detecting portion (3, 4) from a first face (1a) to a second face (1b).

21 Claims, 19 Drawing Sheets

PLASTIC IDENTIFYING APPARATUS AND PLASTIC IDENTIFYING METHOD

TECHNICAL FIELD

The present invention relates to a plastic identifying apparatus and a plastic identifying method for identifying the kinds of plastics to be discarded (in the following, referred to as discarded plastics).

BACKGROUND ART

Conventionally, discarded plastics discarded from households or the like are disposed of by incineration or in landfills. However, incineration and landfills have come to cause social problems such as impact on the global environment and shortages of landfill sites. Accordingly, in recent years, there has been an effort to sort/collect or recycle discarded plastics. In order to recycle the discarded plastics, it is necessary to identify the kinds of discarded plastics.

Conventional methods for identifying the kinds of discarded plastics include, for example, a method utilizing specific gravities. However, the method utilizing specific gravities has had a problem in that plastics are difficult to identify when there is little difference in their specific gravities.

Also, another method for identifying the kinds of discarded plastics is a method utilizing infrared light, for example. As an example of this method utilizing infrared light, the method capable of identifying, for example, plastics whose surface is coated, plastics to which dirt or the like adheres and plastics containing flame retardants in a highly precise manner has been suggested (see JP 2003-202291 A, for example). In this method, a test piece is cut out by punching out a discarded plastic partially, and infrared light is made to enter one face of this test piece (a face corresponding to a surface of the discarded plastic) and the other face, which is different from the above-noted one face (a section taken at the time of forming the test piece (a face exposed for the first time when cut out as the test piece)), while varying a wave number for each face, thereby detecting the intensity (or absorbance) of totally-reflected infrared light corresponding to each wave number. More specifically, as shown in FIG. 15A, for example, a test piece 101 first is held with a chuck 104, and one face of the test piece 101 is brought into close contact with a detection hole (an identifying and detecting portion) 103 for an identifying stage 102 provided in a plastic identifying apparatus. Infrared light is made to enter the one face of the test piece 101 via the identifying and detecting portion 103 so as to identify the one face of the test piece 101. The chuck 104 is provided so as to be rotatable by a rotating portion 105 around an axis of rotation in the horizontal direction (a direction of a plane perpendicular to a B axis direction shown in FIG. 15A) while holding the test piece 101. As shown in FIG. 15B, by rotating the chuck 104 by 90° in a direction indicated by C, another face of the test piece 101 is brought into close contact with the identifying and detecting portion 103, thus identifying this another face. With this method, it becomes possible to identify the surface state of discarded plastics (the kinds of dirt and coating, the degree of degradation and dirt), the kinds of discarded plastics and the kinds of flame retardants that are contained.

However, in the methods and apparatuses of identifying discarded plastics in a highly precise manner by detecting two different faces of a test piece as described above, it has been necessary to hold the test piece with the chuck and rotate the chuck so as to change the test piece face to be analyzed. Thus, in these methods, it has taken time to hold the test piece with the chuck or release it and to rotate the test piece by 90°. Moreover, a large number of processes have been required for identification.

Further, in order to hold the test piece with the chuck, the shape of the test piece is restricted in many ways: for example, the test piece has to be thick enough to be held and has to have a shape adapted for the chuck shape. Moreover, at the time of holding the test piece with the chuck, there has been a risk of dropping the test piece due to chucking error, posing a problem in workability.

DISCLOSURE OF INVENTION

A plastic identifying apparatus according to the present invention is a plastic identifying apparatus for identifying the kind of a plastic in an object to be identified, including an identifying and detecting portion for identifying the kind of the plastic included in the object to be identified, and a toppling system for toppling the object to be identified by applying an external force to the object to be identified in order to change an identification face of the object to be identified facing the identifying and detecting portion.

A plastic identifying method according to the present invention is a plastic identifying method for identifying the kind of a plastic in an object to be identified, including (a) identifying the kind of the plastic included in the object to be identified placed such that a first face of the object to be identified serves as an identification face, using the first face, (b) toppling the object to be identified so as to change the identification face of the object to be identified facing the identifying and detecting portion from the first face to a second face by applying an external force to the object to be identified, (c) identifying the kind of the plastic included in the object to be identified using the second face of the object to be identified, and (d) determining the kind of the plastic included in the object to be identified using an identification result obtained by using the first face and an identification result obtained by using the second face.

DESCRIPTION OF THE INVENTION

Figure 1:
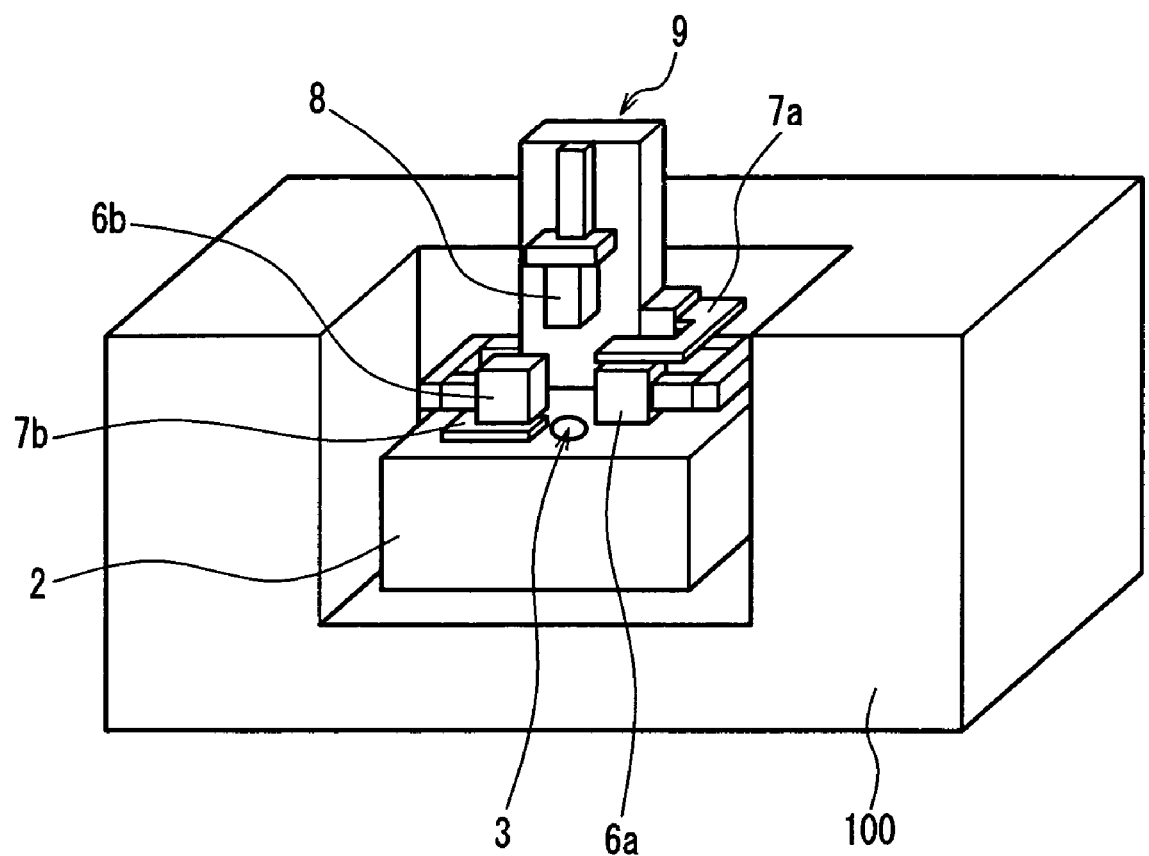
FIG. 1 is a schematic view showing an embodiment of a plastic identifying apparatus according to the present invention.

In a plastic identifying apparatus according to the present invention, a toppling system for toppling an object to be identified applies an external force to the object to be identified, so that a smaller number of processes are needed at the time of changing an identification face of the object to be identified to another face thereof. Thus, identification can be carried out in a short time. Also, since a simple method of applying an external force is adopted, it is possible to achieve a stable workability.

In the plastic identifying apparatus according to the present invention, it is preferable that the object to be identified includes a first face and a second face that are used as the identification face and located adjacent to each other, and in a state where the object to be identified is placed such that the first face faces the identifying and detecting portion as the identification face, the toppling system topples the object to be identified by applying a pushing force to at least a part of an end region of the second face on a side of the first face and at least a part of an end region of a third face, which is opposed to the second face, on a side opposite to the first face, thereby allowing the second face to face the identifying and detecting portion as the identification face. At this time, for example, a pair of pushing members can be used as the toppling system. In the state where the object to be identified is placed so as to face the identifying and detecting portion such that the first face serves as the identification face, it is appropriate that the pair of pushing members be provided so as to be movable in a direction crossing (preferably, perpendicular to) the second face and the third face of the object to be identified and apply the pushing force to the object to be identified by pushing the second face and the third face directly. Also, the toppling system may be a pair of air nozzles, and in the state where the object to be identified is placed so as to face the identifying and detecting portion such that the first face serves as the identification face, it is appropriate that the pair of air nozzles be provided so that their jet tips face the second face and the third face and apply the pushing force to the object to be identified by expelling air from the jet tips toward the second face and the third face of the object to be identified. With the above-described toppling system, the external force can be applied with a simple configuration, thus improving productivity. Incidentally, in the present invention, the magnitude of the pushing force to be applied for toppling the object to be identified is not particularly limited but can be set suitably in the range capable of toppling the object to be identified considering the size of the object to be identified, etc.

The identifying and detecting portion may carry out the identification by allowing an infrared light with a predetermined wave number to enter the object to be identified and detecting an intensity of the infrared light that is totally-reflected by the object to be identified.

The plastic identifying apparatus according to the present invention further may include a pressing portion for pressing the object to be identified so as to bring the object to be identified into close contact with the identifying and detecting portion. The object to be identified is brought into close contact with the identifying and detecting portion using the pressing portion, thereby achieving an identification with even higher precision.

The plastic identifying apparatus according to the present invention further may include a holding portion for holding the object to be identified placed in the identifying and detecting portion. With this holding portion, the object to be identified can be arranged stably at a predetermined position at the time of identification, so that it becomes possible to achieve the identification with even higher precision.

The plastic identifying apparatus according to the present invention may include a first cleaning portion for cleaning a face serving as the identification face of the object to be identified after being toppled. In the case where a holding portion is provided for holding the object to be identified placed in the identifying and detecting portion, this first cleaning portion may be provided in a region in the holding portion facing the face serving as the identification face of the object to be identified after being toppled. Further, the plastic identifying apparatus according to the present invention further may include a second cleaning portion for cleaning the identifying and detecting portion, and this second cleaning portion may be provided in the toppling system. By providing the first cleaning portion and the second cleaning portion as described above, it becomes possible to remove impurities adhering to the identification face of the object to be identified and the identifying and detecting portion, so that the identification can be carried out with even higher precision.

The plastic identifying apparatus according to the present invention further may include an object-to-be-identified positioning portion used for positioning at a time of placing the object to be identified in the identifying and detecting portion. This makes it possible to place the object to be identified in the apparatus in a suitable orientation, so that a face to be identified can be made to face the identifying and detecting portion more reliably.

The plastic identifying apparatus according to the present invention further may include a displacement preventing portion for preventing a displacement of the object to be identified from the identifying and detecting portion by restricting a position of one end portion of the object to be identified when the object to be identified is toppled. This makes it possible to place the object to be identified at a suitable position on the identifying and detecting portion after toppling the object to be identified, so that an identification operation after toppling can be carried out smoothly.

With a plastic identifying method according to the present invention, a smaller number of processes are needed at the time of changing an identification face to another face, so that identification can be carried out in a short time. Also, since a simple method of applying an external force is adopted, it is possible to achieve a stable workability.

In the toppling of the object to be identified in the plastic identifying method according to the present invention, in the case where the second face is adjacent to the first face in the object to be identified, the object to be identified may be toppled by applying a pushing force to at least a part of an end region in the second face on a side of the first face and at least a part of an end region in a third face, which is opposed to the second face, on a side opposite to the first face, thus placing the object to be identified such that the second face serves as the identification face. When applying the pushing force, the second face and the third face may be pushed directly using a pushing member, or air may be blown against the second face and the third face of the object to be identified. By applying these methods, it becomes possible to topple the object to be identified easily.

In identifying in the plastic identifying method according to the present invention, it is preferable that a plastic identifying apparatus including the identifying and detecting portion for identifying the kind of the plastic included in the object to be identified is used, the first face is identified in a state where the first face of the object to be identified is in close contact with the identifying and detecting portion, and the second face is identified in a state where the second face is in close contact with the identifying and detecting portion. With this method, identification with still higher precision becomes possible.

In identifying in the plastic identifying method according to the present invention, the kind of the plastic in the object to be identified may be identified by allowing an infrared light with a predetermined wave number to enter the object to be identified and detecting an intensity of the infrared light that is totally-reflected by the object to be identified.

The toppling of the object to be identified in the plastic identifying method according to the present invention may be started in a state where a third face of the object to be identified is supported. By applying this method, the object to be identified can be prevented from being toppled in a direction opposite to a desired direction.

The plastic identifying method according to the present invention further may include cleaning the second face of the object to be identified before identifying the second face. Also, during the topping of the object to be identified in the plastic identifying method according to the present invention, the identifying and detecting portion may be cleaned. By applying these methods, it becomes possible to remove impurities adhering to the identification face of the object to be identified and the identifying and detecting portion before the identification, so that the identification can be carried out with even higher precision.

In the plastic identifying method according to the present invention, in the case where in the identifying the object to be identified is judged not to be placed at an accurate position with respect to the identifying and detecting portion, an identification operation may be stopped, the object to be identified may be discharged and then the identification operation may be ended.

The following is a description of embodiments of the plastic identifying apparatus and the plastic identifying method according to the present invention, with reference to the accompanying drawings.

Embodiment 1

Figure 2:
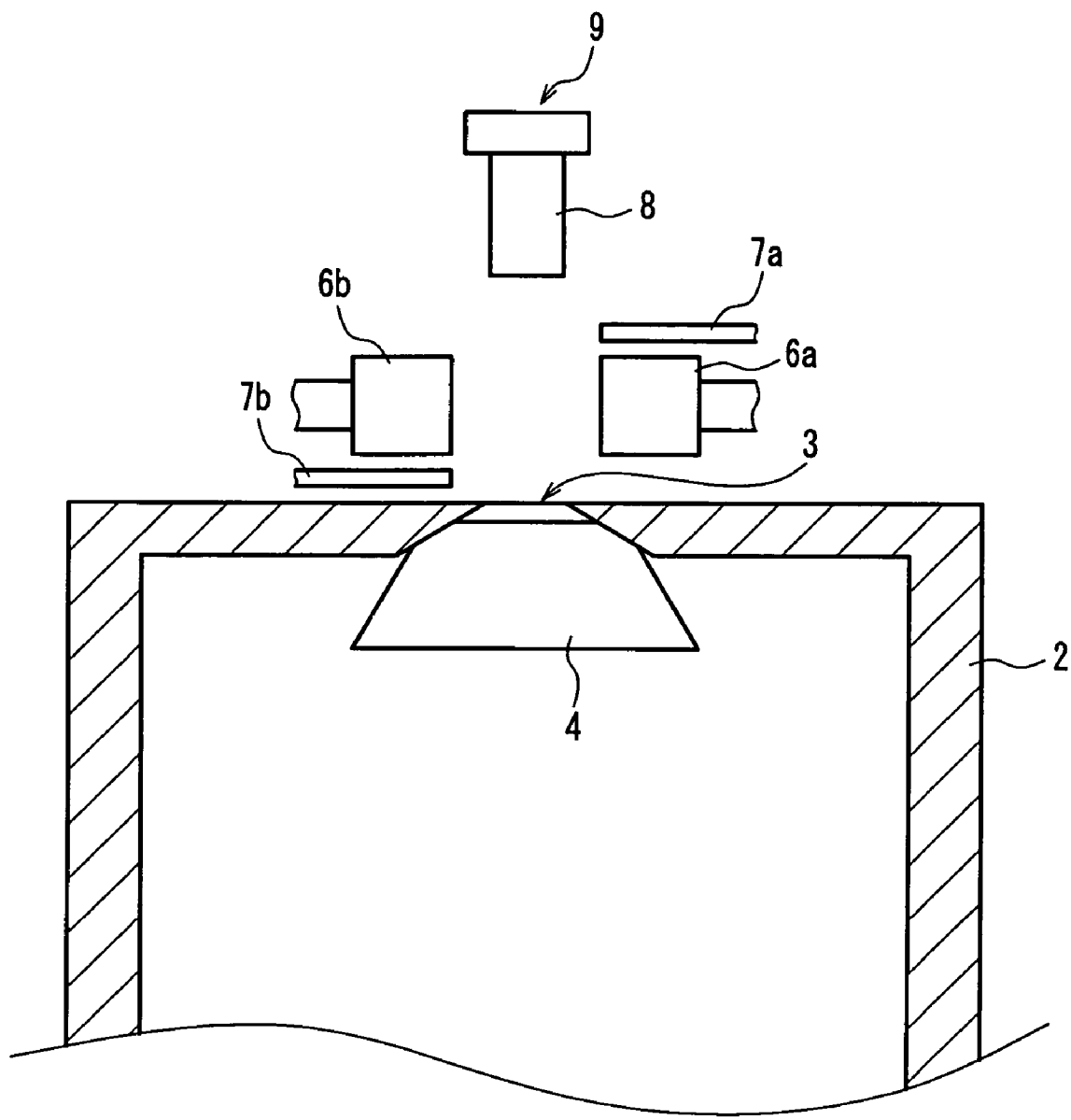
FIG. 2 is a partially sectional schematic diagram showing the plastic identifying apparatus shown in FIG. 1.

FIG. 1 is a schematic view showing the external appearance of a plastic identifying apparatus according to an embodiment of the present invention. FIG. 2 schematically illustrates a configuration of a part in which an object to be identified is placed at the time of an identification operation in the apparatus shown in FIG. 1. For an easier comprehension of each structure of the apparatus, in particular, the structure inside the apparatus, the apparatus shown in FIG. 2 is illustrated partially in cross-section.

In the plastic identifying apparatus and identifying method in the present embodiment, for example, a test piece cut out from a discarded plastic is used as an object to be identified, and at least two faces of this test piece are identified as identification faces. This is because, by identifying each of a first face (for example, a face corresponding to the surface of the object to be identified) and a second face, which is different from the first face (for example, a section taken at the time of forming the test piece (a face exposed for the first time when cut out as the test piece)), the identification can be carried out in a highly precise manner even if the surface of the object to be identified is coated or degraded.

Further, the plastic identifying apparatus according to the present embodiment identifies plastics utilizing infrared light, more particularly, identifies the kinds of plastics included in a test piece by allowing infrared light to enter the test piece and detecting the intensity of the infrared light that is totally-reflected by the test piece (hereinafter, this method is referred to as an infrared light total reflection measurement method in the instant specification).

As shown in FIG. 1, the plastic identifying apparatus in the present embodiment includes an identifying stage 2 provided with a detection hole 3, a holding portion having holding members 6a and 6b for holding a test piece, pushing members 7a and 7b as a toppling system for applying an external force to this test piece so as to topple the test piece sideways, a pressing portion 9 having a presser 8 for bringing the test piece into close contact with the detection hole 3 and a peripheral portion 100 serving to measure the light emission of infrared light and the intensity of reflected infrared light and analyze them. More specifically, as shown in FIG. 2, this plastic identifying apparatus is provided with a prism 4 that is built into the identifying stage 2 and allows infrared light with a predetermined wave number to enter from the detection hole 3 to the test piece. The infrared light that has entered is totally-reflected by the test piece, and after passing through the prism 4 again, its intensity is measured. Although not shown in FIG. 2, a sampled test piece is placed on the identifying stage 2 such that its identification face faces the detection hole 3. Thus, in the plastic identifying apparatus according to the present embodiment, the prism 4 and the detection hole 3 that function for allowing infrared light to enter the test piece correspond to an identifying and detecting portion. In the instant specification, for convenience, only the detection hole 3 sometimes is described as the identifying and detecting portion.

In the case of using the above-noted infrared light total reflection measurement method, it is possible to identify the kinds of plastics included in the test piece more precisely even when the test piece includes dark-colored plastics or flame retardants. It should be noted that the infrared light with a predetermined wave number described above is light whose wave number ranges from 400 cm$^{-1}$ to 4000 cm$^{-1}$, for example. When identifying the kinds of plastics included in the test piece, it is appropriate to allow infrared light to enter the test piece while varying the wave number and detect the intensity (or absorbance) of the totally-reflected infrared light according to each wave number. Alternatively, utilizing Fourier transform infrared (FT-IR) spectroscopy, the intensity (or absorbance) of the totally-reflected infrared light for the above-noted predetermined wave number also may be detected. For example, the wavelength-intensity distributions for predetermined plastics may be stored in advance in, for instance, a control portion (not shown) provided in the peripheral portion 100 and then compared with the wavelength-intensity distribution obtained by the above-mentioned detection, thereby identifying the kinds of plastics included in the test piece easily.

Further, as described above, the plastic identifying apparatus according to the present embodiment includes the holding portion having the holding members 6a and 6b for holding a test piece from both lateral surfaces when the test piece is placed in the identifying and detecting portion, namely, placed over the detection hole 3 of the identifying stage 2, the pushing members 7a and 7b as the toppling system for applying an external force to the test piece and the pressing portion 9 having the presser 8 for bringing the test piece into close contact with the identifying and detecting portion. The holding portion includes a movable system (not shown) for allowing a pair of the holding members 6a and 6b to move in a substantially horizontal direction. By moving the holding members 6a and 6b in the horizontal direction with this movable system, it is possible to hold the placed test piece from both lateral surfaces. The pressing portion 9 includes a movable system (not shown) for allowing the presser 8 to be raised and lowered. By raising and lowering the presser 8 with this movable system, it is possible to bring the test piece into close contact with the identifying and detecting portion at the time of identification. The detailed operation of the pushing members 7a and 7b will be described later.

Now, referring to FIGS. 3 to 7, an identification operation will be described. FIGS. 3 to 7 are schematic diagrams showing how a test piece 1 is identified using the apparatus shown in FIGS. 1 and 2. The test piece 1 is formed as an object to be identified by punching with a punch press, for example. Herein, a first face 1a (the section at the time of forming the test piece in this case) and a second face 1b (the surface of the object to be identified) of the test piece 1 serve as the identification faces.

Figure 3:
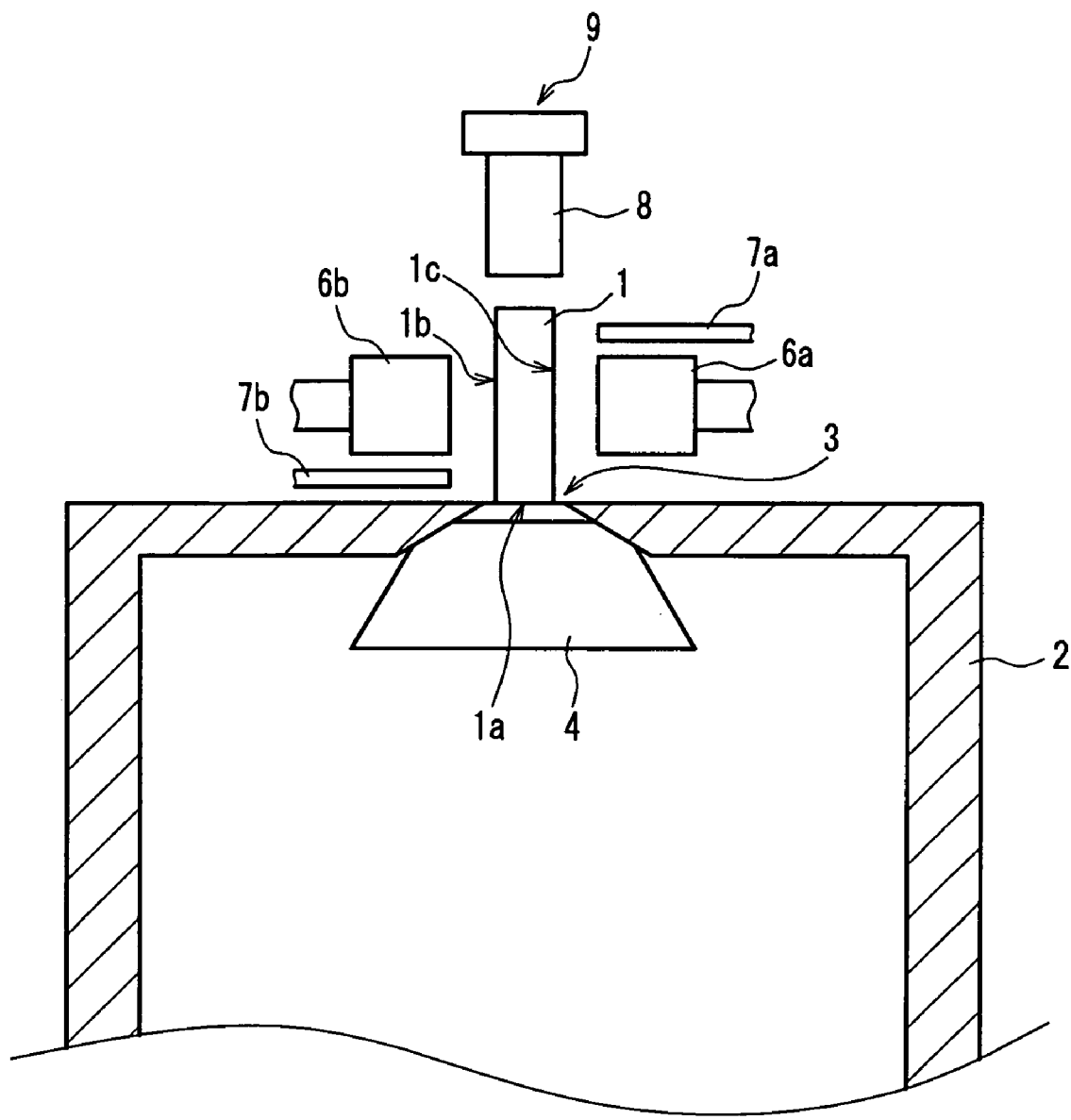
FIG. 3 is a partially sectional schematic diagram showing how a test piece is placed in the plastic identifying apparatus shown in FIG. 1.

First, as shown in FIG. 3, the test piece 1 is supplied to the plastic identifying apparatus. The test piece 1 is arranged so that the first face 1a as the identification face faces the detection hole 3 serving as the identifying and detecting portion and the second face 1b, which is the next identification face, faces to the left in the figure.

Figure 4:
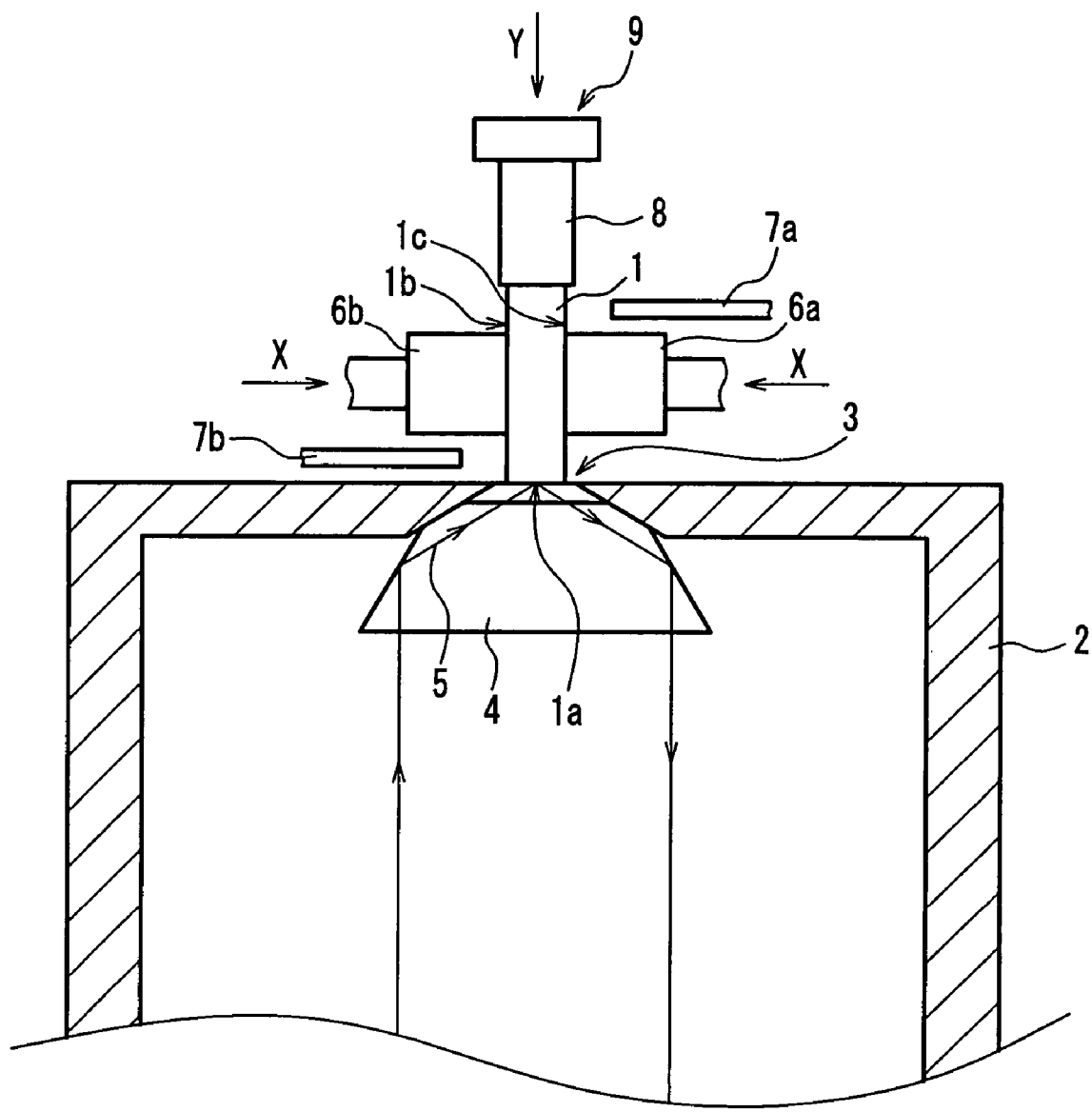
FIG. 4 is a partially sectional schematic diagram showing how a first face of the test piece is identified using the plastic identifying apparatus shown in FIG. 1.

Next, as shown in FIG. 4, the holding members 6a and 6b are moved in the horizontal direction (directions indicated by X in the figure) so as to hold the test piece 1 from both lateral surfaces, and further the presser 8 is lowered (moved in a direction indicated by Y) so as to press the test piece 1 from above, thereby bringing the first face 1a into close contact with the identifying and detecting portion (the detection hole 3). Thereafter, infrared light 5 is made to enter the first face 1a of the test piece 1, and the intensity of the infrared light that has been totally-reflected by the test piece 1 and passed through the prism 4 again is measured, thus carrying out the identification.

Figure 5:
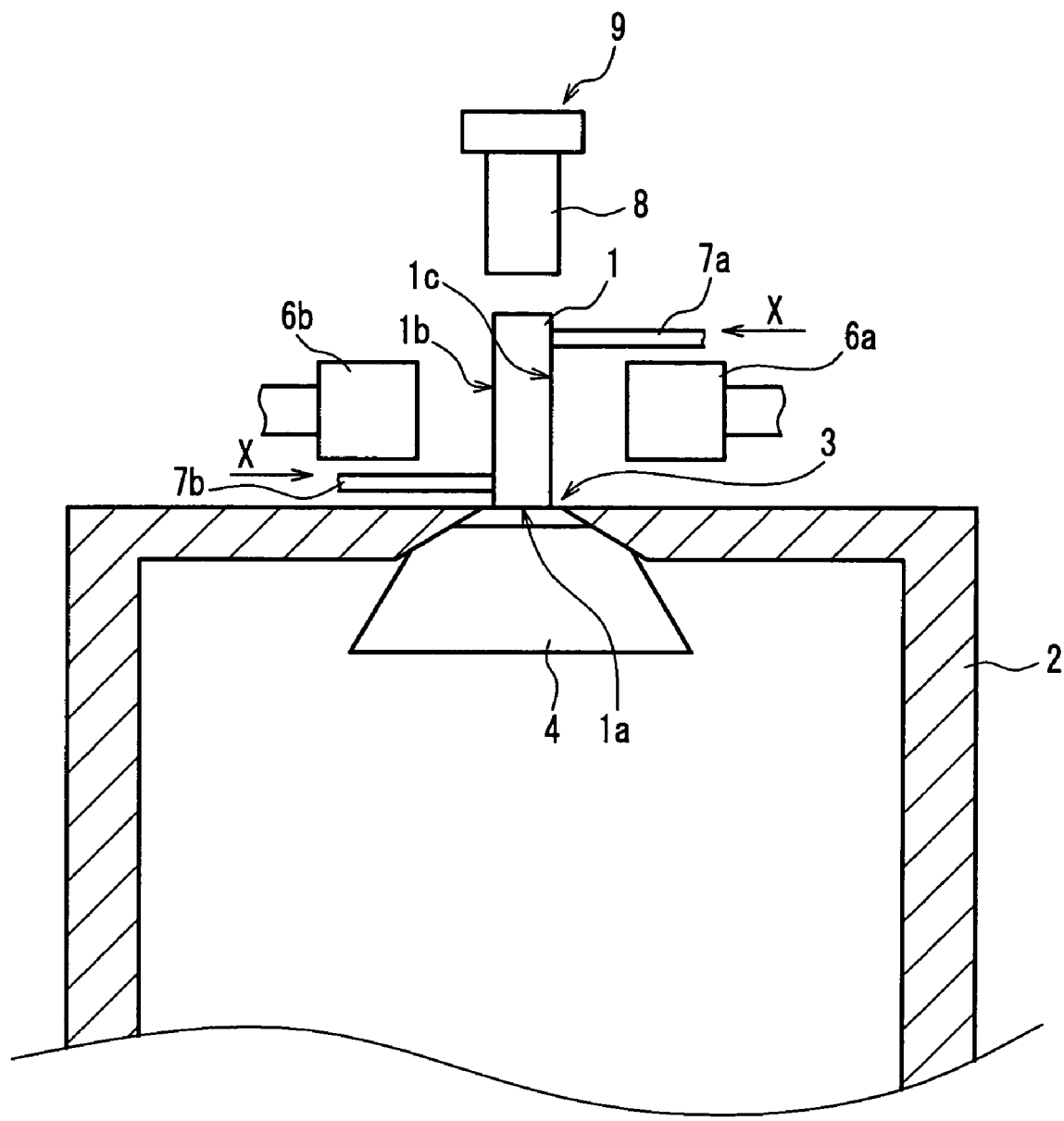
FIG. 5 is a partially sectional schematic diagram showing how a pushing force is applied to the test piece using the plastic identifying apparatus shown in FIG. 1.
Figure 6:
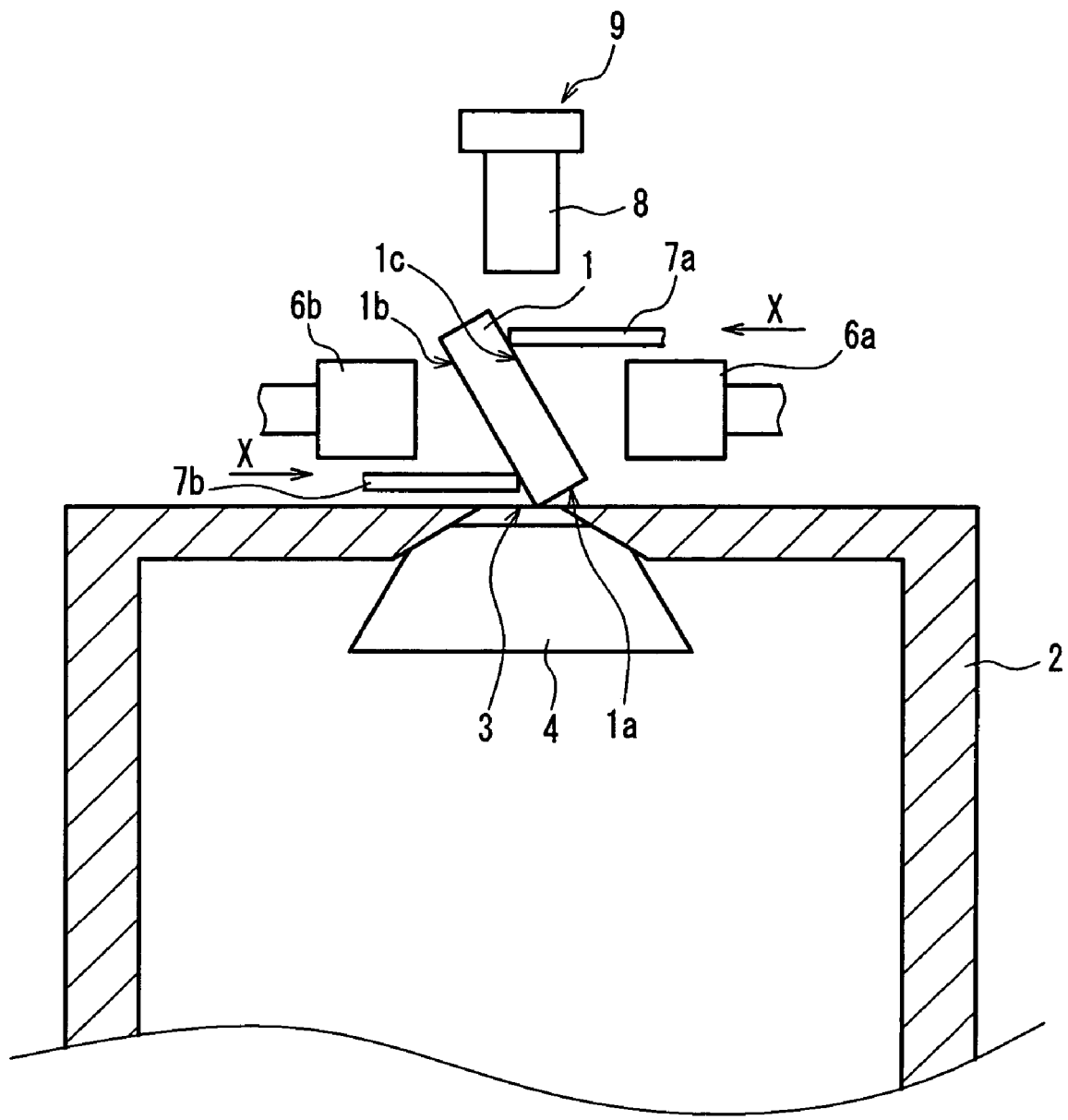
FIG. 6 is a partially sectional schematic diagram showing how the test piece is toppled using the plastic identifying apparatus shown in FIG. 1.

Next, as shown in FIGS. 5 and 6, in order to shift the test piece 1 to change the identification face, an operation of toppling the test piece 1 is conducted. This toppling operation is carried out so that, after the toppling, the test piece 1 is placed on the detection hole 3 in such a manner that the second face 1b serving as the next identification face is located over the detection hole 3. More specifically, the pushing members 7a and 7b are moved in substantially the horizontal direction (the directions indicated by X in FIG. 5), while the holding portion and the pressing portion 9 are released to move the holding members 6a and 6b and the presser 8 away from the test piece 1. These pushing members 7a and 7b are provided so as to be movable by a movable system, which is not shown in the figure, in the substantially horizontal direction (directions substantially perpendicular to the lateral surfaces of the test piece 1 (the second face 1b and a third face 1c opposed to this face)), with the pushing member 7b on the side of the second face 1b, which is the next identification face, being located at a position corresponding to a lower end portion (a part of an end region on the side of the first face 1a) of the second face 1b and the pushing member 7a on the side of the third face 1c being located at a position corresponding to an upper end portion (a part of an end region on the side opposite to the first face 1a) of the third face 1c. By pressing the pushing members 7a and 7b, pushing forces are applied to the lower end portion of the second face 1b and the upper end portion of the third face 1c, respectively. These pushing forces serve as a force to topple the test piece 1, and the test piece 1 is toppled so that the second face 1b contacts the identifying and detecting portion as shown in FIG. 6.

Figure 7:
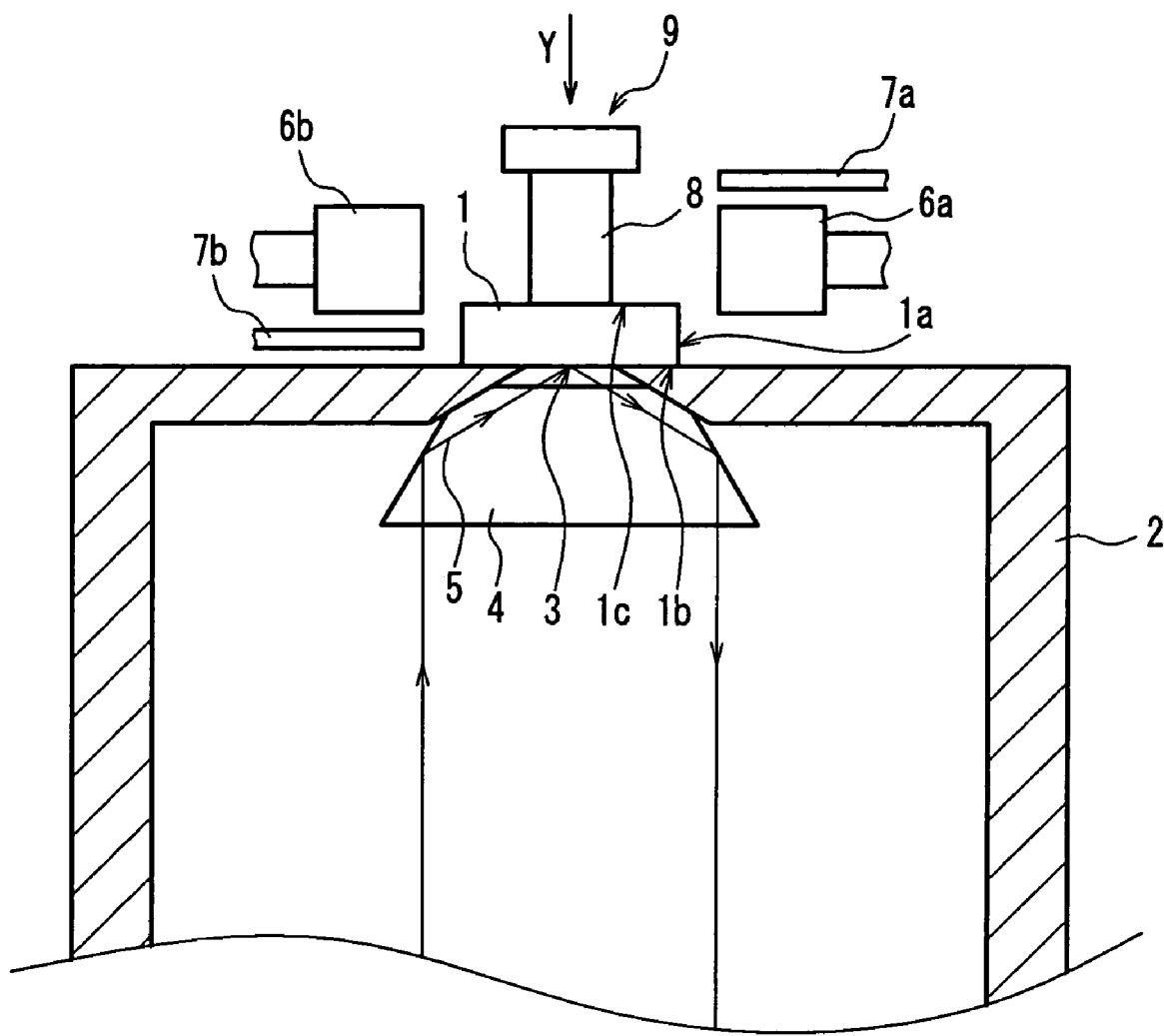
FIG. 7 is a partially sectional schematic diagram showing how a second face of the test piece is identified using the plastic identifying apparatus shown in FIG. 1.

Thereafter, as shown in FIG. 7, the pressing portion 9 is operated again so as to lower the presser 8, thereby bringing the second face 1b of the test piece 1 into close contact with the identifying and detecting portion. In this state, the infrared light 5 is made to enter the second face 1b, thus identifying the second face 1b. It should be noted that, since the second face 1b of the test piece 1 has a larger area than the first face 1a thereof in this case, the test piece can be arranged stably even if it is not held using the holding portion, and therefore, the holding portion is not operated here. In this way, it is appropriate that the holding portion should be operated suitably considering the shape of the test piece 1, the size of the identification face, etc.

As described above, in accordance with the plastic identifying apparatus in the present embodiment, two faces of the test piece can be identified with a small number of processes and a simple operation in a highly precise manner within a short time. Also, since there is less restriction in the shape of the test piece, it is possible to achieve versatility and stable workability. It should be noted that the shapes of the pushing members 7a and 7b are not limited to those shown in FIG. 1 but may be a flat-plate shape, a rod shape or the like as long as a pushing force can be applied directly to the test piece 1.

Figure 8:
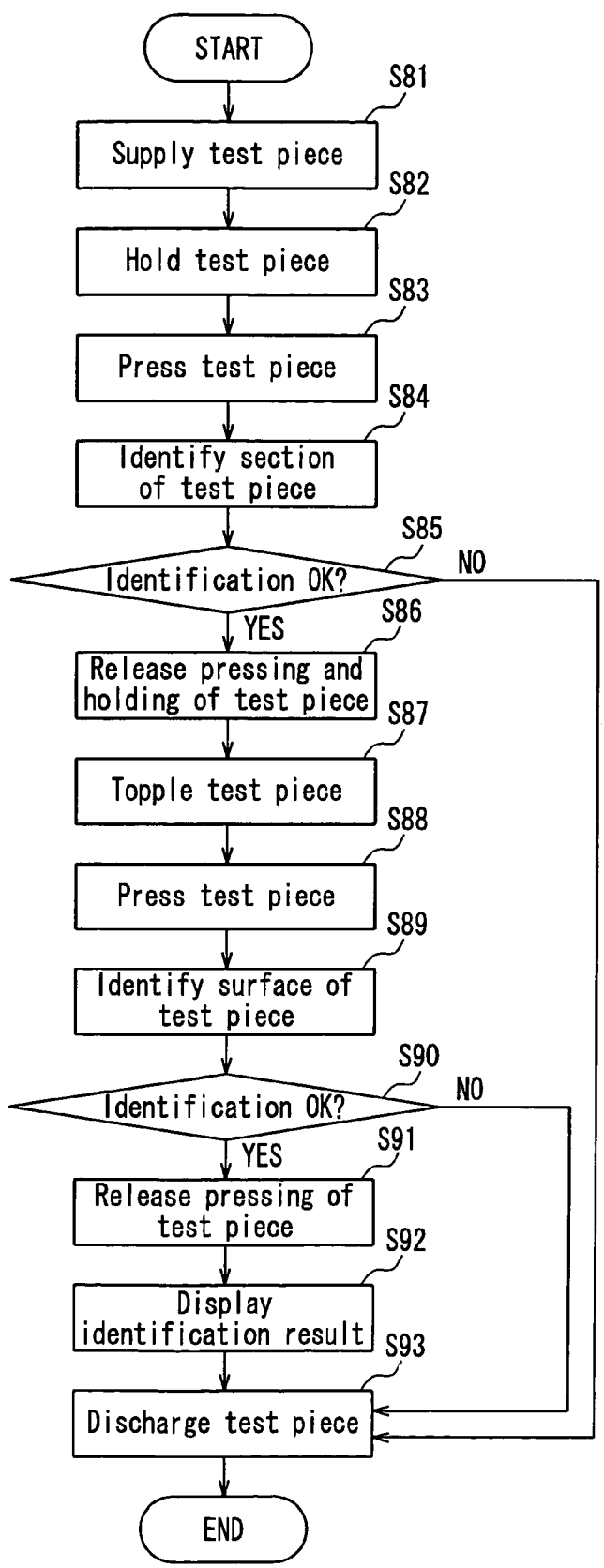
FIG. 8 is a flowchart showing an example of a plastic identifying method according to the present invention.

Further, it also is possible to provide the plastic identifying apparatus according to the present embodiment with a function of dealing with the case in which the test piece cannot be placed properly on the identifying and detecting portion. By providing such a function, a continuous identification operation can be carried out more smoothly. For example, it is appropriate to provide a function of moving to the next step if the test piece is judged to be identifiable and discharging the test piece if it is judged not to be identifiable. The judgment of whether or not the test piece is identifiable is made by, for example, detecting whether or not the test piece is in contact with the identifying and detecting portion with a pressure-sensitive sensor provided in the identifying and detecting portion. Alternatively, the judgment also can be made by detecting whether or not there is any clearance between the identifying and detecting portion and the test piece with an infrared ray sensor provided around the identifying and detecting portion. FIG. 8 shows a flowchart of the identification operation in this case. First, the test piece is supplied to the apparatus (Step (in the following, simply referred to as S) 81). Next, the holding portion and the pressing portion are operated so as to hold the test piece and press the test piece to bring it into close contact with the identifying and detecting portion (S82 and S83). Incidentally, the holding portion and the pressing portion may be operated substantially simultaneously. Subsequently, the first face (the section in this case) of the test piece is identified (S84), and whether or not the identification has been carried out accurately is judged (S85). If it has, then the pressing portion and the holding portion are released (S86), thus performing an operation of toppling the test piece (S87) and pressing the test piece (S88) and an operation of identifying the second face (the surface of the object to be identified in this case) (S89). Next, whether or not the second face has been identified accurately also is judged (S90). If it has, then the pressing of the test piece is released (S91) and the result of identification is displayed (S92), followed by discharging the test piece (S93). If it is judged that the test piece has not been identified accurately in S85 and S90, the test piece is discharged, and the identification operation is ended. The test piece can be discharged by, for example, providing an air nozzle or the like so that air can be blown against the test piece from one side, thus discharging the test piece to the other side.

Embodiment 2

The following is a description of another embodiment of the plastic identifying apparatus and the plastic identifying method according to the present invention. The plastic identifying apparatus of the present embodiment has a configuration similar to the plastic identifying apparatus shown in FIGS. 1 and 2 described in Embodiment 1 but has a partially different operation.

Figure 9:
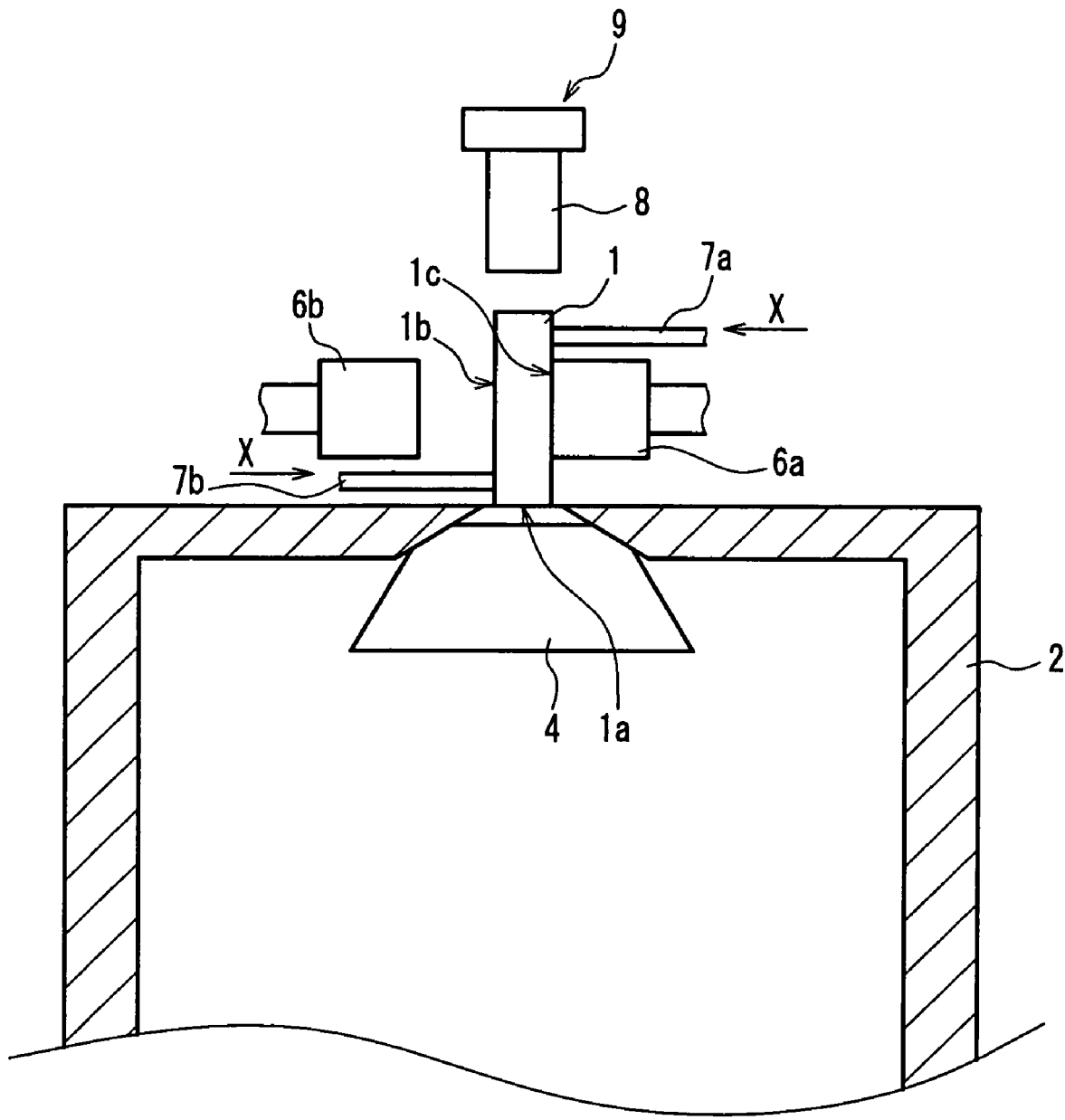
FIG. 9 is a partially sectional schematic diagram showing another example at the time of applying a pushing force to the test piece using the plastic identifying apparatus shown in FIG. 1.

FIG. 9 shows how the pushing force starts to be applied to the test piece 1. Unlike Embodiment 1 (see FIG. 5), in the plastic identifying apparatus according to the present embodiment, the holding member 6a on the side of the third face 1c alone is allowed to contact the test piece 1 when the pushing force starts to be applied to the test piece 1. If the holding members 6a and 6b are both released (moved away from the test piece 1) before operating the pushing members 7a and 7b, the test piece 1 might be toppled in the opposite direction, so that the second face 1b, which is the face that should be identified, could not be brought into contact with the identifying and detecting portion. On the other hand, by supporting the test piece 1 from the side of the third face 1c using the holding member 6a as described above, it becomes possible to topple the test piece 1 more reliably such that the second face 1b contacts the identifying and detecting portion. In the case of such an operation, the holding member 6a is released immediately after the pushing members 7a and 7b come into contact with the test piece 1 and the pushing force starts to be applied.

Embodiment 3

The following is a description of yet another embodiment of the plastic identifying apparatus and the plastic identifying method according to the present invention. The plastic identifying apparatus of the present embodiment has a configuration similar to the plastic identifying apparatus shown in FIGS. 1 and 2 described in Embodiment 1 except that a first cleaning portion for cleaning the test piece and a second cleaning portion for cleaning the identifying and detecting portion are provided further.

Figure 10A:
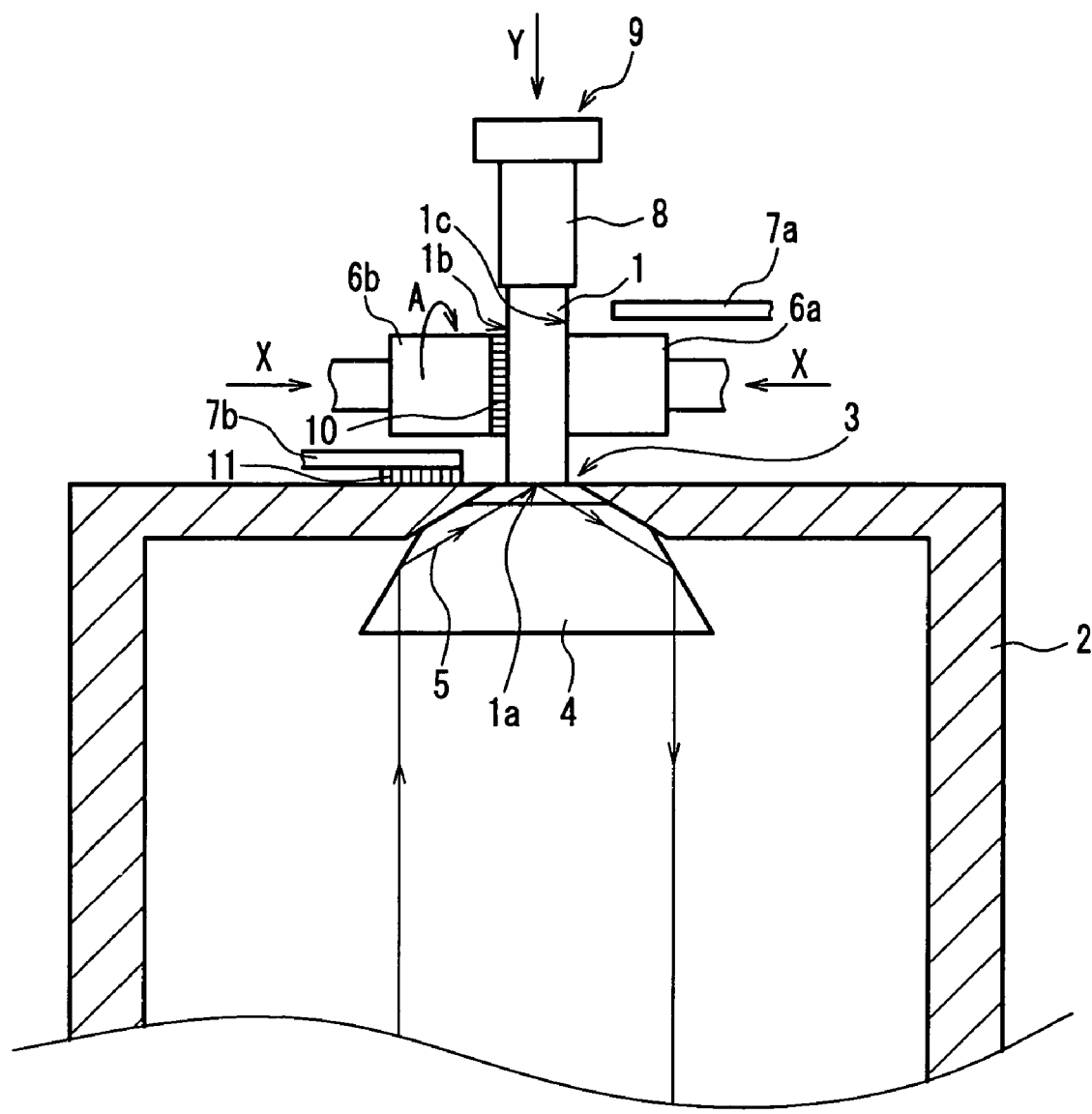
FIG. 10A is a partially sectional schematic diagram showing how an identification face of the test piece is cleaned using a plastic identifying apparatus provided with a first cleaning portion for cleaning the identification face of the test piece and a second cleaning portion for cleaning an identifying and detecting portion in another embodiment of the plastic identifying apparatus according to the present invention.
Figure 10B:
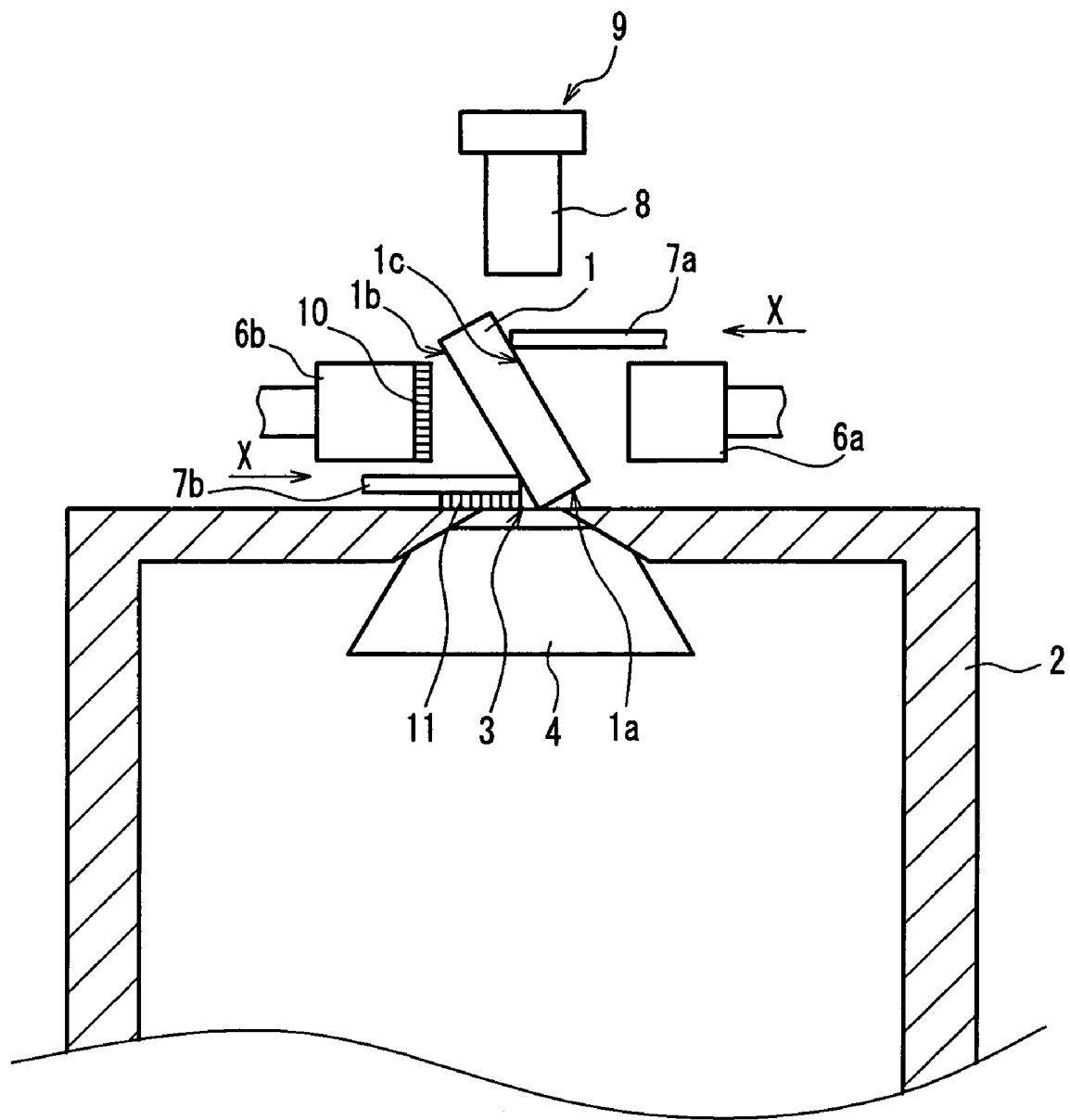
FIG. 10B is a partially sectional schematic diagram showing how the second cleaning portion cleans the identifying and detecting portion at the time of toppling the test piece using the plastic identifying apparatus shown in FIG. 10A.

FIGS. 10A and 10B show how the test piece and the identifying and detecting portion are cleaned with the plastic identifying apparatus according to the present embodiment. The first cleaning portion includes a brush 10 provided in a tip portion of the holding member 6b on the side of the second face 1b of the test piece 1. In this case, the holding member 6b is provided rotatably, and by rotating this holding member 6b in a direction indicated by A in the figure together with the brush 10 at the tip, it is possible to clean the second face 1b serving as the identification face after being toppled (see FIG. 10A).

The second cleaning portion includes a brush 11 provided on the side of the identifying stage 2 of the pushing member 7b on the side of the second face 1b. By providing the second cleaning portion in this manner, the pushing member 7b is moved in the X directions in the figure during the toppling operation, thereby cleaning the identifying and detecting portion simultaneously (see FIG. 10B).

As described above, providing the first and second cleaning portions makes it possible to identify the test piece 1 precisely even in the case where impurities such as dirt adhere to the surface of the test piece 1 and the identifying and detecting portion. It should be noted that the first and second cleaning portions may be in any form as long as they can clean the surface of the test piece and the identifying and detecting portion. Thus, these cleaning portions may be provided as members different from the holding member 6b and the pushing member 7b or can be a cloth or a sponge instead of a brush.

Embodiment 4

The following is a description of yet another embodiment of the plastic identifying apparatus and the plastic identifying method according to the present invention. The plastic identifying apparatus of the present embodiment has a configuration similar to the plastic identifying apparatus shown in FIGS. 1 and 2 described in Embodiment 1 except that an object-to-be-identified positioning portion for positioning at the time of placing the test piece on the apparatus is provided further.

Figure 11A:
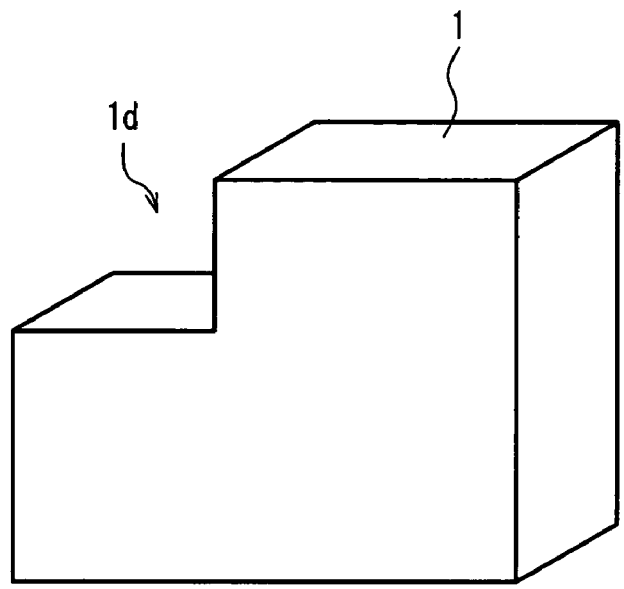
FIGS. 11A and 11B are perspective views showing test pieces having a cut-out portion used for positioning when the test piece is placed in the plastic identifying apparatus.
Figure 11B:
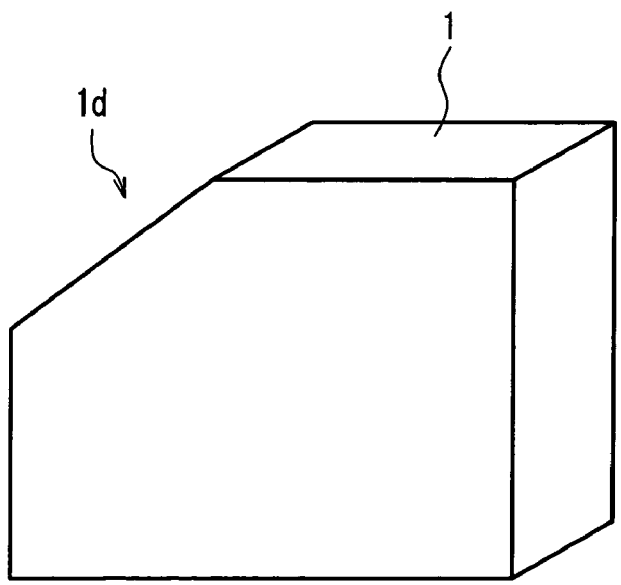
Figure 12A:
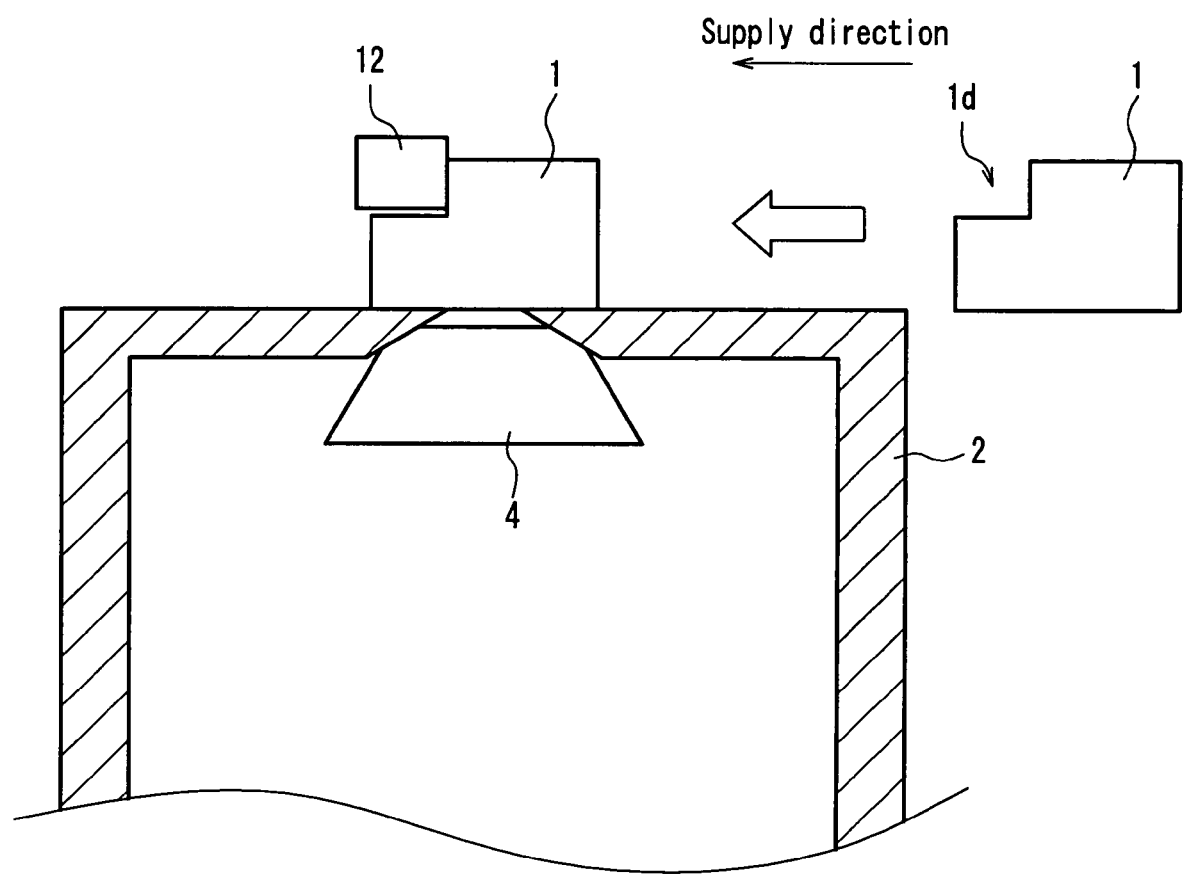
FIGS. 12A and 12B are partially sectional schematic diagrams showing how the test pieces shown in FIGS. 11A and 11B are supplied to the plastic identifying apparatus.
Figure 12B:
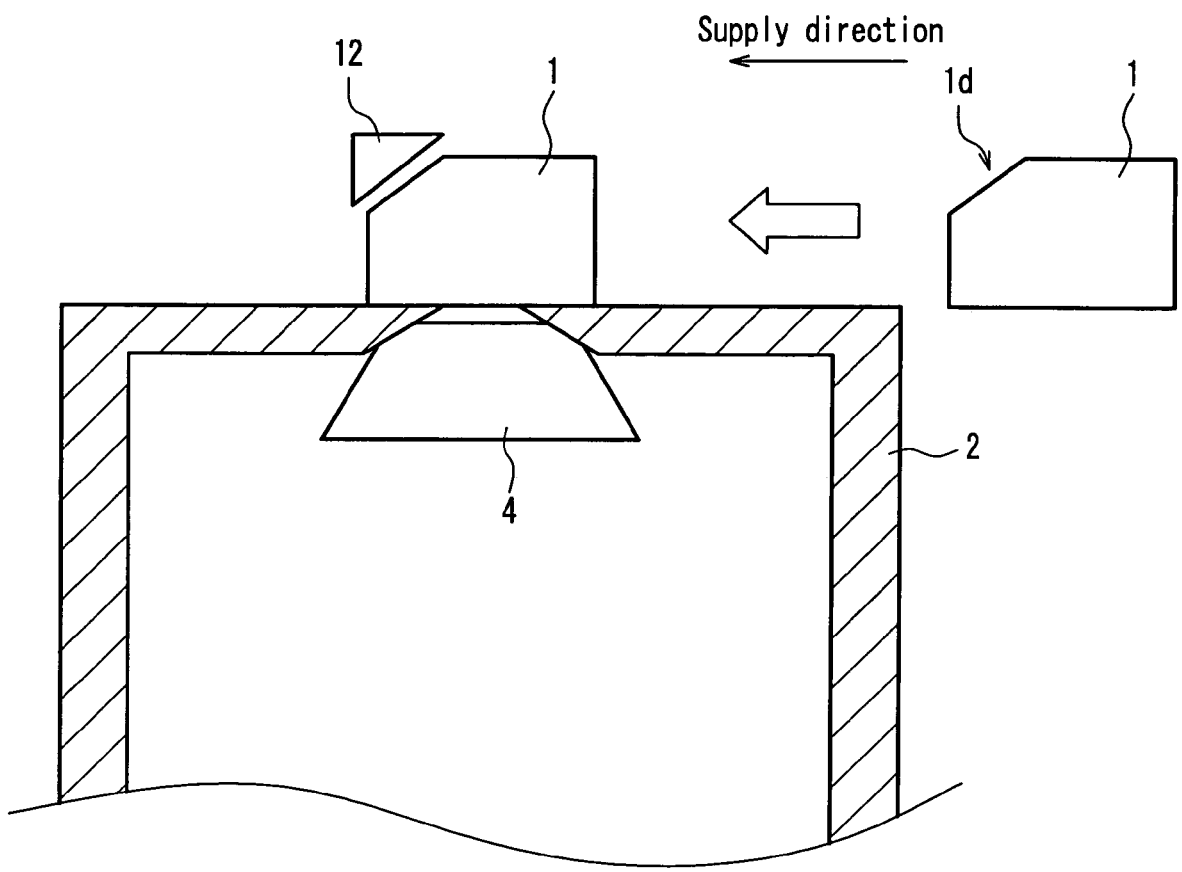

In the case of using the plastic identifying apparatus according to the present embodiment, the test piece 1 is provided with a cut-out portion 1d as shown in FIGS. 11A and 11B, for example. The position of this cut-out portion 1d is determined so as to correspond to the position of the object-to-be-identified positioning portion of the plastic identifying apparatus. The plastic identifying apparatus according to the present embodiment is provided with an object-to-be-identified positioning portion 12 as shown in FIGS. 12A and 12B, for example, and by aligning the cut-out portion 1d of the test piece 1 with the object-to-be-identified positioning portion 12, it is possible to supply the test piece 1 in an accurate orientation.

With the above-described configuration, an error in the orientation of supplying the test piece 1 can be prevented, so that a face to be identified (the second face of the test piece in this case) can be brought into contact with the identifying and detecting portion more reliably when toppling the test piece 1. Incidentally, the shape of the cut-out portion 1d of the test piece 1 shown in FIGS. 11A and 11B and the shape of the object-to-be-identified positioning portion 12 shown in FIGS. 12A and 12B are merely an example and should not be taken as limiting.

Embodiment 5

The following is a description of another embodiment of the plastic identifying apparatus and the plastic identifying method according to the present invention. The plastic identifying apparatus of the present embodiment has a configuration similar to the plastic identifying apparatus shown in FIGS. 1 and 2 described in Embodiment 1 but has a partially different operation.

Figure 13A:
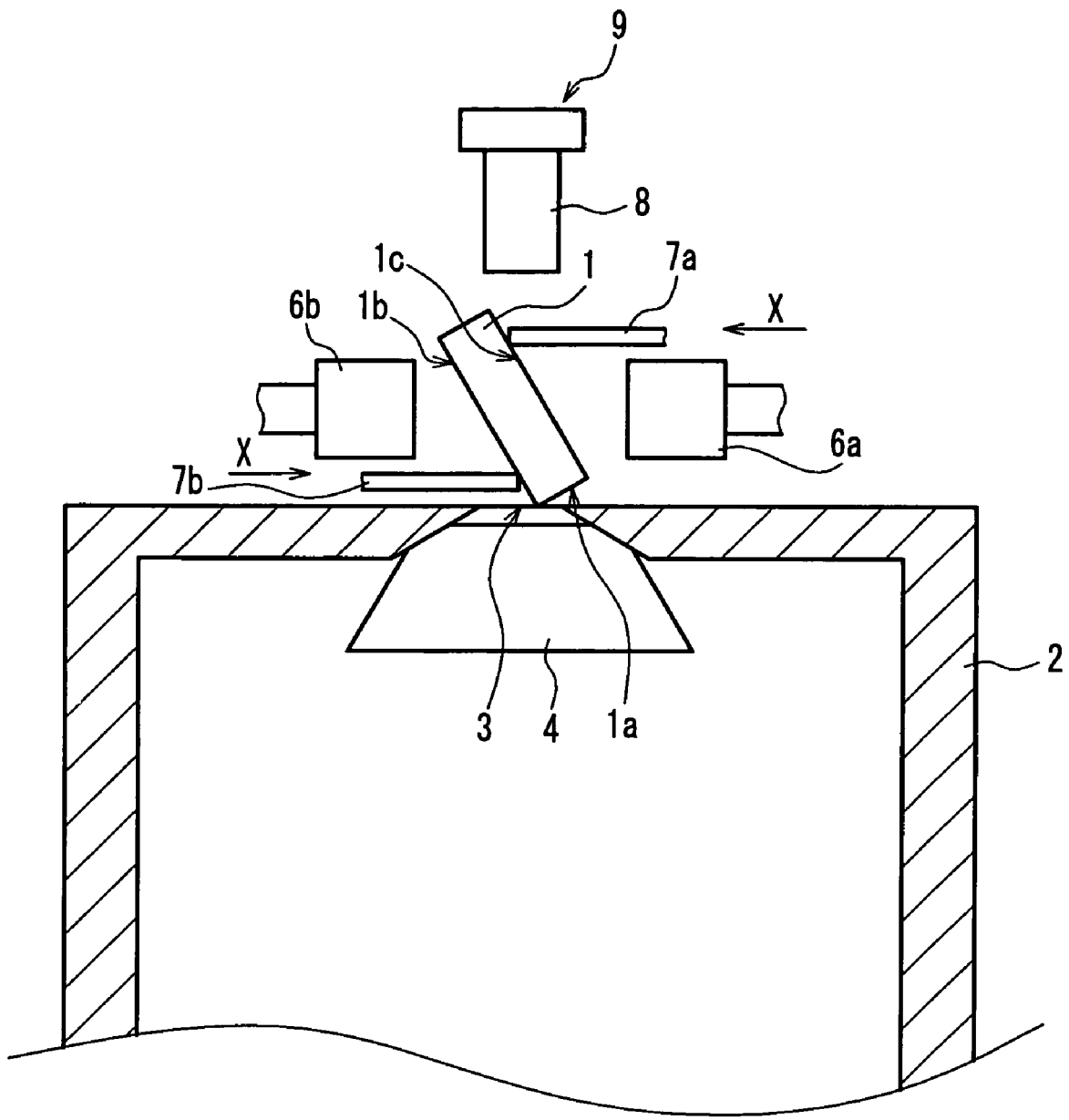
FIGS. 13A to 13C are partially sectional schematic diagrams showing how a displacement is prevented when toppling a test piece using a plastic identifying apparatus provided with a displacement preventing portion in another embodiment of the plastic identifying apparatus according to the present invention.
Figure 13B:
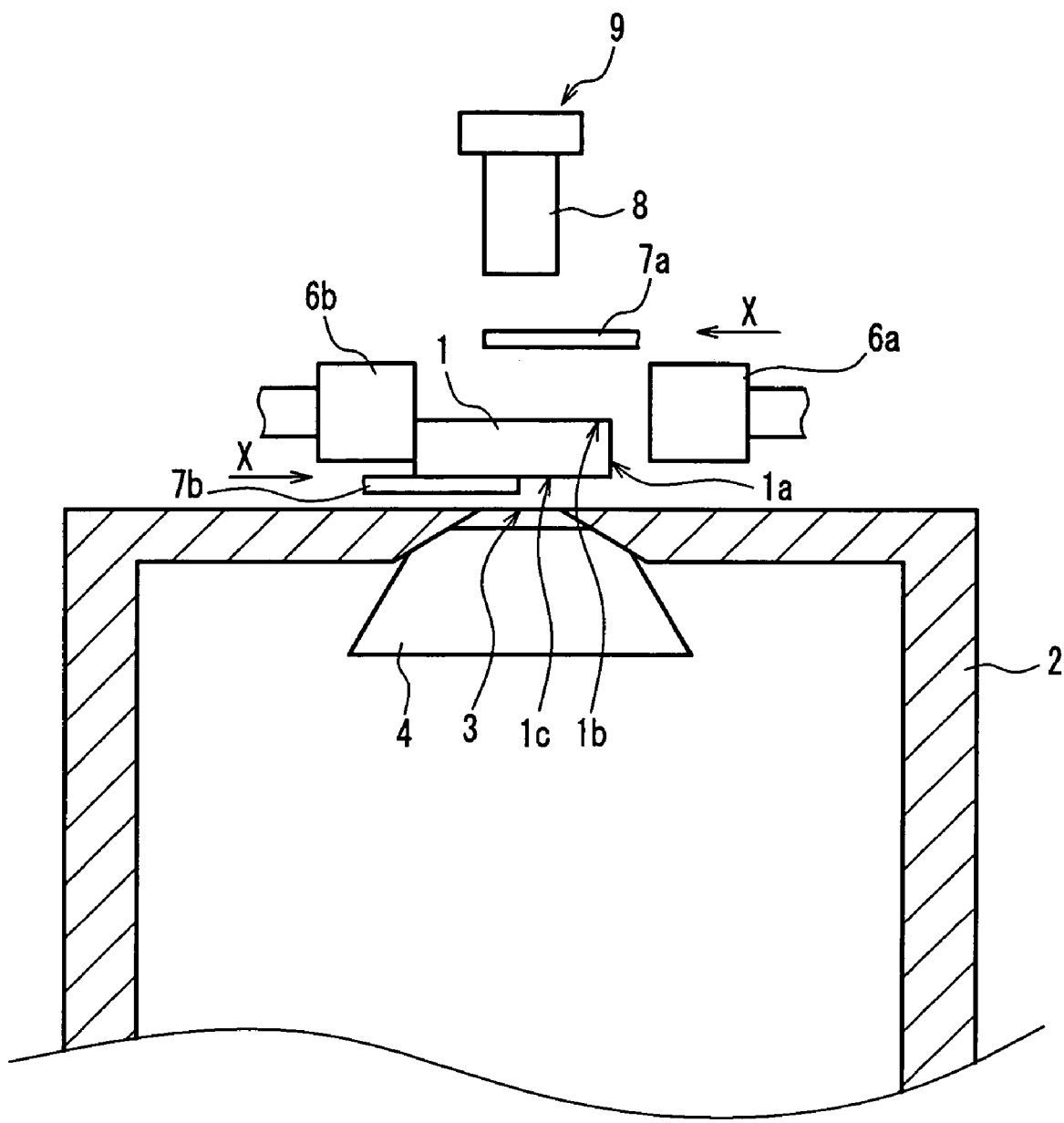
Figure 13C:
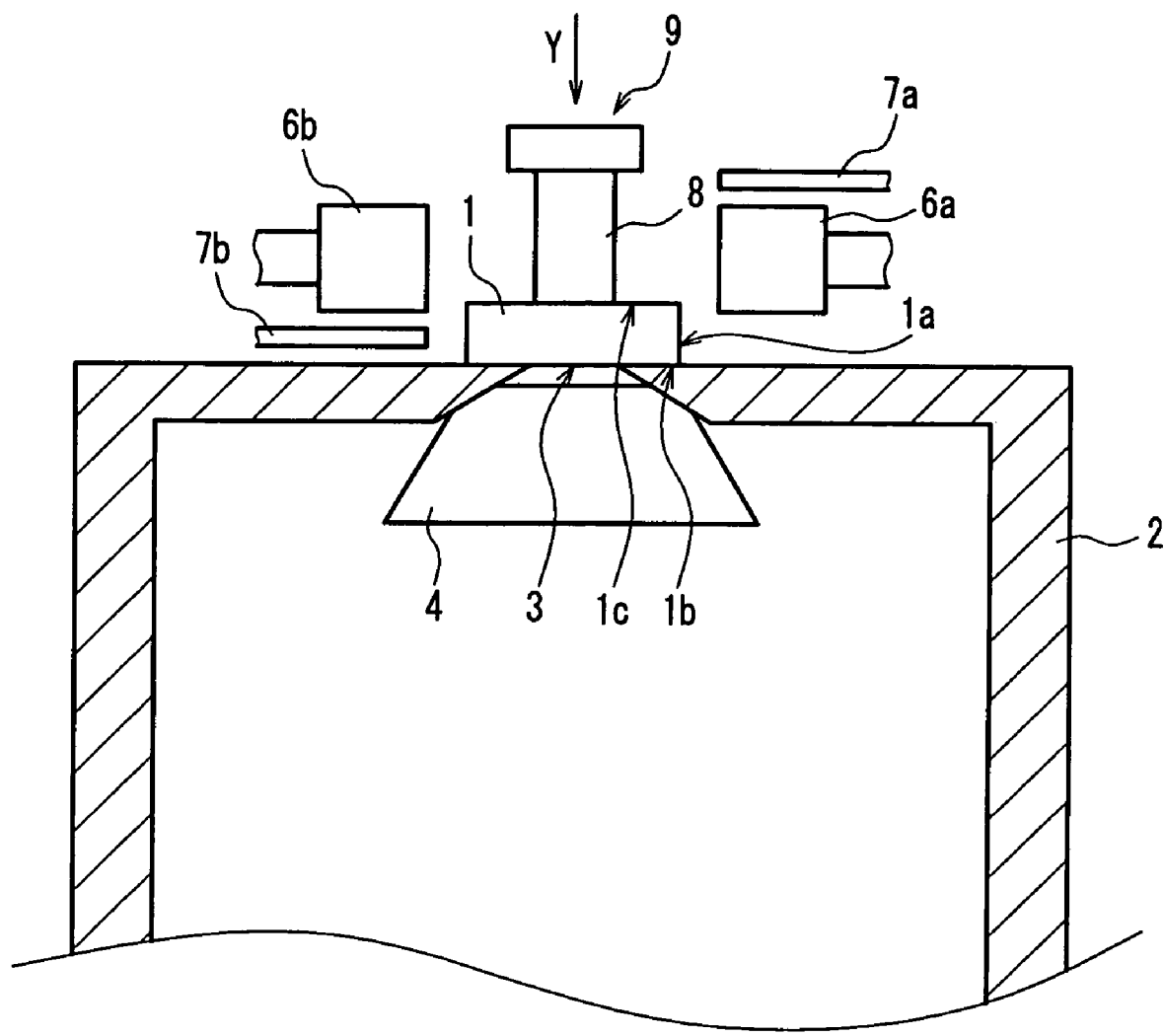

In the plastic identifying apparatus according to the present embodiment, the holding member 6b on the side of the second face 1b of the test piece 1 also has a function as a displacement preventing portion for preventing the displacement of the test piece 1 when toppling the test piece 1. FIGS. 13A to 13C show how the displacement preventing portion provided in the plastic identifying apparatus according to the present embodiment prevents the displacement at the time of toppling the test piece. In the present embodiment, after the test piece 1 is toppled using the pushing members 7a and 7b as shown in FIG. 13A, the holding member 6b is arranged at a predetermined position in contact with an end portion of the test piece 1 so as to restrict the position of the test piece 1 (see FIGS. 13B and 13C). The holding member 6b is made to function as the displacement preventing portion in this manner, whereby even when the toppled test piece 1 falls onto the pushing member 7b as shown in FIG. 13B, for example, the test piece 1 can be dropped from the pushing member 7b onto the detection hole 3 on the identifying stage 2 and placed at a predetermined position as shown in FIG. 13C.

Embodiment 6

The following is a description of yet another embodiment of the plastic identifying apparatus and the plastic identifying method according to the present invention. The plastic identifying apparatus of the present embodiment has a configuration similar to the plastic identifying apparatus shown in FIGS. 1 and 2 described in Embodiment 1 except that the pushing members are replaced by air nozzles as the toppling system.

Figure 14:
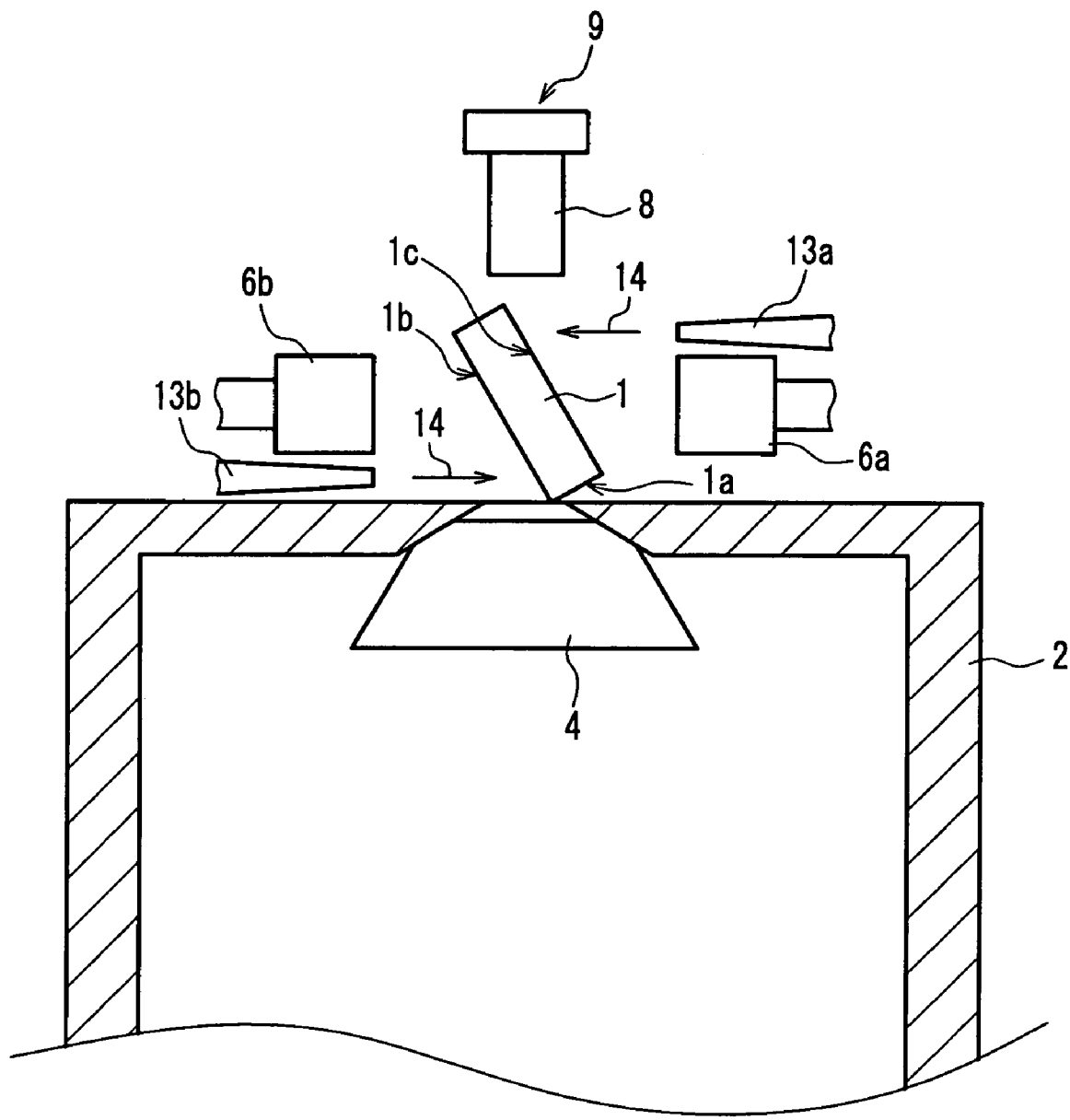
FIG. 14 is a partially sectional side view showing how a test piece is toppled using a plastic identifying apparatus in yet another embodiment of the plastic identifying apparatus according to the present invention.
Figure 15A:
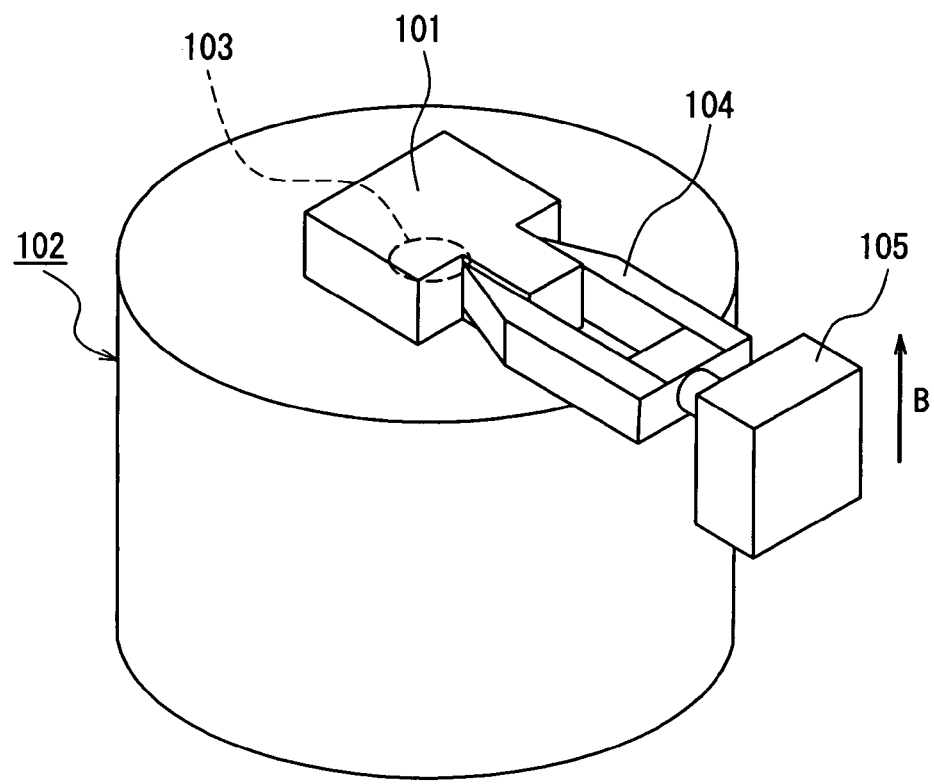
FIGS. 15A and 15B are schematic views showing an operation of rotating a test piece with a chuck in a conventional plastic identifying apparatus.
Figure 15B:
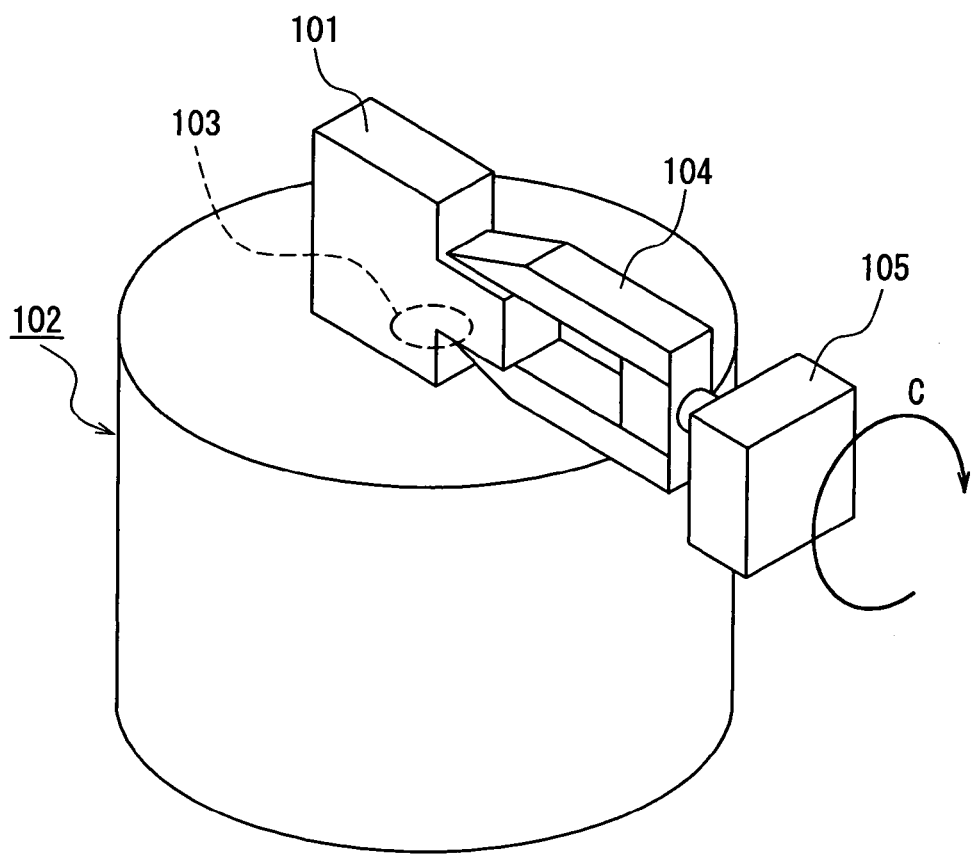

FIG. 14 shows how the test piece 1 is toppled using the plastic identifying apparatus according to the present embodiment. In the present embodiment, air nozzles 13a and 13b are provided instead of the pushing members and allowed to expel an air toward the second face 1b and the third face 1c, thus applying a pushing force. In this manner, the configuration of using the air nozzles 13a and 13b as the toppling system also makes it possible to apply a pushing force to the test piece 1 and topple the test piece 1 similarly to Embodiment 1. Further, with this configuration, it also is possible both to reduce the cycle time for operating the toppling system and to suppress problems such as the test piece 1 falling onto the toppling system. Furthermore, after discharging the test piece, these air nozzles 13a and 13b also can function as the second cleaning portion for cleaning the identifying and detecting portion.

In Embodiments 1 to 6 described above, the description has been directed to the case of identifying plastics included in an object to be identified by the infrared light total reflection measurement method. However, it also is possible to use other measurement methods.

INDUSTRIAL APPLICABILITY

In accordance with a plastic identifying apparatus and a plastic identifying method of the present invention, it is possible to identify the kinds of plastics in a highly precise manner within a short time and achieve high versatility and excellent workability owing to less restriction on a test piece shape.

The invention claimed is:

1. A plastic identifying apparatus for identifying a kind of a plastic in an object to be identified comprising a first face and a second face that are used as an identification face and located adjacent to each other, the plastic identifying apparatus comprising:
    an identifying and detecting portion for identifying the kind of the plastic included in the object to be identified; and
    a toppling system for toppling the object to be identified by applying an external force to the object to be identified in order to change the identification face of the object to be identified facing the identifying and detecting portion;
    wherein in a state where the object to be identified is placed such that the first face faces the identifying and detecting portion as the identification face, the toppling system topples the object to be identified by applying a pushing force to at least a part of an end region of the second face on a side of the first face and at least a part of an end region of a third face, which is opposed to the second face, on a side opposite to the first face, thereby allowing the second face to face the identifying and detecting portion as the identification face.

2. The plastic identifying apparatus according to claim 1, wherein the toppling system is a pair of pushing members, and
    in the state where the object to be identified is placed such that the first face faces the identifying and detecting portion as the identification face, the pair of pushing members are provided so as to be movable in a direction crossing the second face and the third face of the object to be identified and apply the pushing force to the object to be identified by pushing the second face and the third face directly.

3. The plastic identifying apparatus according to claim 1, wherein the toppling system comprises a pair of air nozzles, and
    in the state where the object to be identified is placed such that the first face faces the identifying and detecting portion as the identification face, the pair of air nozzles are provided so that their jet tips face the second face and the third face and apply the pushing force to the object to be identified by expelling an air from the jet tips toward the second face and the third face of the object to be identified.

4. The plastic identifying apparatus according to claim 1, wherein the identifying and detecting portion allows an infrared light with a predetermined wave number to enter the object to be identified and detects an intensity of the infrared light that is totally-reflected by the object to be identified.

5. The plastic identifying apparatus according to claim 1, further comprising a pressing portion for pressing the object to be identified so as to bring the object to be identified into close contact with the identifying and detecting portion.

6. The plastic identifying apparatus according to claim 1, further comprising a holding portion for holding the object to be identified placed in the identifying and detecting portion.

7. The plastic identifying apparatus according to claim 1, further comprising a first cleaning portion for cleaning a face serving as the identification face of the object to be identified after being toppled.

8. The plastic identifying apparatus according to claim 7 further comprising a holding portion for holding the object to be identified placed in the identifying and detecting portion, and the first cleaning portion is provided in a region in the holding portion facing the face serving as the identification face of the object to be identified after being toppled.

9. The plastic identifying apparatus according to claim 1, further comprising a second cleaning portion for cleaning the identifying and detecting portion.

10. The plastic identifying apparatus according to claim 9, wherein the second cleaning portion is provided in the toppling system.

11. The plastic identifying apparatus according to claim 1, further comprising an object-to-be-identified positioning portion used for positioning at a time of placing the object to be identified in the identifying and detecting portion.

12. The plastic identifying apparatus according to claim 1, further comprising a displacement preventing portion for preventing a displacement of the object to be identified from the identifying and detecting portion by restricting a position of one end portion of the object to be identified when the object to be identified is toppled.

13. A plastic identifying method for identifying a kind of a plastic in an object to be identified, comprising:
  (a) identifying the kind of the plastic included in the object to be identified placed such that a first face of the object to be identified serves as an identification face, using the first face;
  (b) toppling the object to be identified so as to change the identification face of the object to be identified facing an identifying and detecting portion from the first face to a second face by applying an external force to the object to be identified,
  (c) identifying the kind of the plastic included in the object to be identified using the second face of the object to be identified; and
  (d) determining the kind of the plastic included in the object to be identified using an identification result obtained by using the first face and an identification result obtained by using the second face;
  wherein in the (b) toppling, the second face is adjacent to the first face in the object to be identified, and the object to be identified is toppled by applying a pushing force to at least a part of an end region in the second face on a side of the first face and at least a part of an end region in a third face, which is opposed to the second face, on a side opposite to the first face, thus placing the object to be identified such that the second face serves as the identification face.

14. The plastic identifying method according to claim 13, wherein in the (b) toppling, the pushing force is applied to the object to be identified by pushing the second face and the third face directly using a pushing member.

15. The plastic identifying method according to claim 13, wherein in the (b) toppling, the pushing force is applied to the object to be identified by blowing an air against the second face and the third face of the object to be identified.

16. The plastic identifying method according to claim 13, wherein in the (a) identifying and the (c) identifying, a plastic identifying apparatus comprising the identifying and detecting portion for identifying the kind of the plastic included in the object to be identified is used,
  the (a) identifying is performed in a state where the first face of the object to be identified is in close contact with the identifying and detecting portion, and
  the (c) identifying is performed in a state where the second face of the object to be identified is in close contact with the identifying and detecting portion.

17. The plastic identifying method according to claim 13, wherein in the (a) identifying and the (c) identifying, the kind of the plastic in the object to be identified is identified by allowing an infrared light with a predetermined wave number to enter the object to be identified and detecting an intensity of the infrared light that is totally-reflected by the object to be identified.

18. The plastic identifying method according to claim 13, wherein the (b) toppling is started in a state where a third face of the object to be identified is supported.

19. The plastic identifying method according to claim 13, further comprising cleaning the second face of the object to be identified between the (a) identifying and the (b) toppling.

20. The plastic identifying method according to claim 13, wherein in the (b) toppling, the identifying and detecting portion is cleaned.

21. The plastic identifying method according to claim 13, wherein in the (a) identifying and the (c) identifying, an identification operation is stopped and the object to be identified is discharged if the object to be identified is judged not to be placed at an accurate position with respect to the identifying and detecting portion.

* * * * *